United States Patent [19]

Grosskopf

[11] 4,420,768

[45] Dec. 13, 1983

[54] METHOD AND APPARATUS FOR THE DETECTION OF ACCUMULATIONS OF PARTICLES SUCH AS METAPHASE PLATES

[75] Inventor: Rudolf Grosskopf, Konigsbronn, Fed. Rep. of Germany

[73] Assignee: Carl-Zeiss-Stiftung, Heidenheim, Fed. Rep. of Germany

[21] Appl. No.: 324,586

[22] Filed: Nov. 24, 1981

[30] Foreign Application Priority Data

Nov. 28, 1980 [DE] Fed. Rep. of Germany ....... 3044883

[51] Int. Cl.³ ............................................. H04N 7/18
[52] U.S. Cl. ...................................... 358/107; 377/10
[58] Field of Search .................... 358/107; 235/92 PC, 235/92 MP; 377/3, 53, 24, 10, 11; 356/335; 382/6

[56] References Cited

U.S. PATENT DOCUMENTS 3,720,812  3/1973  Downs ................................ 358/107
3,922,532  11/1975  Kitchener et al. .................. 358/107
3,967,053  6/1976  Grosskopf .......................... 358/107
4,047,205  9/1977  Grosskopf .......................... 358/107

Primary Examiner—Howard Britton
Assistant Examiner—Edward L. Coles
Attorney, Agent, or Firm—Hopgood, Calimafde, Kalil, Blaustein & Judlowe

[57] ABSTRACT

For the detection of accumulations of particles, for instance metaphase plates, in an image converted by a raster process into electrical signals, there is first effected an electronic dilation in several directions, the parameters of the dilation being so selected that images of the chromosomes of the metaphase plates agglomerate to form unitary structures. Thereupon, an electronic erosion of images is effected in several directions, the parameters of the erosion being so selected that images of cells and impurities disappear but the agglomerated metaphase-plate images are retained. A circuit is described which consists essentially of length discriminators, decision-logic devices, delay-storage devices with provision for establishing input digital preset values, in which circuit the entire evaluation process takes place with the speed of the scanning process.

18 Claims, 3 Drawing Figures

METHOD AND APPARATUS FOR THE DETECTION OF ACCUMULATIONS OF PARTICLES SUCH AS METAPHASE PLATES

BACKGROUND OF THE INVENTION

The present invention relates to a method of detecting accumulations of particles, for instance metaphase plates, as the same may be caused to be viewable in a microscope image, wherein the image is converted by a raster process into raster elements which are electronically scanned, treated, and evaluated, using decision logic to determine whether each individual raster element fits or does not fit the criteria for which an evaluation is sought.

In order to measure the size, shape and number of desired particles or other features of a flat image of the character indicated, this image is scanned in raster-form by a beam of light or electrons. Electric signals are thereby produced in a receiver such as a photocell, a photomultiplier or a television camera. These scanning signals are fed for evaluation to a so-called discriminator which produces binary signals, of time duration corresponding to line-scanned chord length in the objects to be evaluated.

For better digital evaluation, a generator is used to produce a high frequency voltage, and this generator is synchronized with movement of the scanning beam (U.S. Pat. No. 2,494,941, West German Provisional Patent AS 1,423,636). This generator supplies a voltage which divides the image or the scan lines into individual raster elements.

For further processing of the digitalized image which has been divided into raster elements, various methods are known, under the name "texture analysis".

German Pat. No. 2,128,690 describes a device for the texture analysis of a non-homogeneous object. The device contains logical-analysis and counter circuitry to recognize and count such objects. This device contains a circuit arrangement by means of which it is decided whether an image-structure element fits predetermined criteria for the object under examination; to this end, delay-storage devices and comparators are used. The storage devices delay incoming image signals for periods of time which correspond on the one hand to the distance between two raster elements of one line each, and which correspond on the other hand approximately to a line length. In the comparators, actual values of image signals which lie alongside of each other in different directions are compared with each other, to thereby give information concerning the entire content of the structure element. Upon the evaluation, the structure element is displayed stepwise along the scanning lines in the image examined, an output signal being produced, for instance, when the structure element is located completely within an image particle.

U.S. Pat. No. 3,967,053 describes an arrangement in which each raster element has an associated preset digital value which, within the limits of each object to be evaluated, is decremented one bit at a time in at least one pre-selected direction in successive scanning lines until a pre-selected guide or criteria value is reached. The only image signals which pass for further evaluation are those for which a raster element has an associated preset signal value which accords with the guide value. By selective connection of delay members, delay time is established to determine the displacement of raster elements in successive lines and thus the direction of length discrimination.

Devices of the character indicated have long been used for automatic evaluation of the most varied structures and are useful in many fields of application. However, they are not sufficiently efficient for detection of very complex structures. Thus, for example, for automatic detection of metaphase plates, the recent trend has been to use methods in which digitalized image signals are fed immediately to a computer for further processing. While it is true that almost any complex program can be processed in a computer, the fact remains that, even with relatively simple programs, computer-processing times become too great, unless one uses an extremely large computer system which is too expensive for routine instruments. In searching for metaphase plates, traditional computers or microprocessor circuits are either too expensive or are not sufficiently efficient, so that the sampling of preparations is too time-consuming.

Metaphase plates are accumulations of chromosomes (of a cell) which accumulations are the product of a special technique by which they have been separated from other components of the cell. In good metaphase plates, the chromosomes are distributed over a surface which is considerably larger than one cell. In poor metaphase plates, the chromosomes "stick" to each other and cover a surface which is only slightly larger than one cell.

In biology and medicine, the automatic detection of metaphase plates is gaining increasing importance. Practical uses are the detection of genetic damage in early pregnancy (amniocentesis) and successive investigations of radiation damage. In the latter case particularly, it is necessary to evaluate a very large number of metaphase plates, which must previously be found on a slide beneath a microscope. There are practical applications in which more than 99% of the surface on a slide contains uninteresting cells and impurities; less than 1% of the surface, typically 0.1% of the surface, has metaphase plates suitable for evaluation.

GENERAL DESCRIPTION OF THE INVENTION

The object of the present invention is to provide an inexpensive rapidly operating method which functions with the same speed as a scanning system and permits differentiation between impurities, cells, and other undesired disturbing elements on the one hand, and accumulations of particles of interest, particularly metaphase plates, on the other hand, and which thus relieves the biologist or physician from having to conduct a tedious search for metaphase plates.

The invention achieves this object by employing electronic texture-analysis apparatus in conjunction with microscope viewing of specimen slides; and in the particular case of searching for metaphase plates, the texture analysis is in the context of performing an electronic dilation in each of several directions, the parameters of the dilations being so selected that the chromosomes of metaphase plates agglomerate to form uniform structures; whereupon an electronic erosion is performed in each of several directions, the parameters of the erosions being so selected that the cells disappear from the image while the agglomerated metaphase plates remain.

The method of the invention will be described below using metaphase plates as the illustrative example. However, the invention applies in general to accumulations of any particles of interest insofar as they differ sufficiently from the other objects, in respect of size and distribution.

For the method of the invention, it is advisable first of all to effect an electronic erosion in several directions on all objects in the image, the parameters being so selected that at least by far the greatest number of the images of impurities disappear while the images of chromosomes are retained. Thereupon, in a second step, an electronic dilation is effected in several directions, the parameters of the dilation being so selected that the images of chromosomes of metaphase plates grow together to form unitary structures. Since the chromosomes of a metaphase plate are distributed over a larger area than corresponds to the surface of individual cells, structures are thus formed which can be clearly distinguished by their size from the cells, which have become only slightly larger. Thereupon, in a third step, an erosion is again effected using parameters so selected that the cell images disappear but the images of agglomerated metaphase plates are retained; in performing this step, images of impurities which were not previously removed because of their size are also removed (insofar as the impurities are not larger than cells). After the third step, only the images of agglomerated metaphase plates are still present. Their size is a measure of their quality since in good metaphase plates the chromosomes lie further apart than in poor ones. Accordingly, the indicated method makes it possible not only to find metaphase plates but also to effect a rough evaluation. The latter, however, does not replace a more accurate examination, which can then be carried out but which is no longer an object of the present invention.

The method of the present invention is by no means limited to the arrangement for erosion or dilation indicated in said U.S. Pat. No. 3,967,053; the invention will, however, be described using a circuit which is based on the one described in said patent, but it will be understood that other individual circuit modules or circuits with microprocessors can also be employed. First of all, however, the fundamental construction of apparatus will be described, for performing the method of the invention.

A specimen slide beneath a microscope is scanned in known manner with a television camera or by a laser beam. The scanning can be carried out, for instance, by shifting the preparation on a microscope stage within the observation-ray path of the microscope, from image field to image field of a television camera, so that gradually and progressively the entire surface of the object is scanned. Alternatively, in a known flying-spot technique, the light spot formed by a laser can be moved back and forth on the object via mirrors or other deflection means, and the image signal may be detected by a radiation receiver. The manner of operation with a laser, in contradistinction to a television camera, permits continuous scanning of a strip on the slide without being bound in each case to the image frequency or to the number of lines of the television camera.

In contradistinction to the methods customary in microprocessor circuits and in electronic evaluation circuits for comparison of old information with newly added information, the arrangement of the invention, in one particularly advantageous embodiment, is based on the arrangement described in said U.S. Pat. No. 3,967,053, in the interest of speedy evaluation and simple construction. Advantage for the stated object results from the fact that decision-logic and delay-storage devices are scanned with a clock frequency which corresponds to the image-spot frequency of the scanning process. In this way, it is possible to have stored information from each preceding line available at the output of its storage when the scanning beam reaches the line location which is in adjacent offset relation to the corresponding line location in the previous line. As a result, the entire evaluation process takes place with the speed of the scanning process. The evaluation process is accordingly substantially faster than evaluation in a computer. Further advantage resides in the lower expense for delay-storage devices, which results from the decrementing of a digital preset value for each raster element.

For a simple order-of-magnitude analysis in a direction oblique to the scan-line direction, the transmission of information from prior lines is shown in FIG. 3b of the said AS 2,354,769 provisional patent; for erosion in three directions, the procedure is explained in connection with FIGS. 4 and 5 of said patent. For the present task, additional circuit components are necessary.

In one particularly advantageous embodiment of the invention, the detection of metaphase plates is realized by providing components behind the discriminator which converts analog signals into binary signals, these components including a first electronic image-erosion circuit module, consisting of a length discriminator in the scan-line direction, and one decision-logic device (with an associated delay-storage device) for each of the scanning directions down-right and down-left; a first inverter (which inverts all image signals so that a second module, after a second inversion, can effect an electronic dilation of the image objects); the second circuit module consists of a length discriminator in the scan-line direction, and one decision-logic device (with an associated delay-storage device) for each of the scanning directions down-right and down-left; the second inverter; and a third image-erosion circuit module consists of a length discriminator in the scan-line direction, and one decision-logic device (with an associated delay-storage device) for each of the scanning directions down-right and down-left. All length-discriminating components are preferably equipped with means for the inputting of digital preset values and guide values. The image signals which leave the last such component of the last module are fed to an evaluation unit which then performs, in known manner, a size analysis of the metaphase plates which remain in the image.

If it is found in the evaluation unit that a metaphase plate is present, this is reported to a control unit which controls the entire course of the measurement, including movement of the scanning table, etc. The control unit then provides an output indication of the corresponding coordinates, in suitable manner.

In one advantageous embodiment of the invention, the discriminator output is furthermore connected to one or more image-storage devices. When the output unit has found at least one metaphase plate in an image, the control unit causes transfer of the image information to an evaluation-computer which effects a detailed examination.

Further advantageous embodiments of the arrangement of the invention will appear from the description below.

DETAILED DESCRIPTION

The invention will be described in detail in conjunction with the accompanying drawings, in which.

Figure 1:
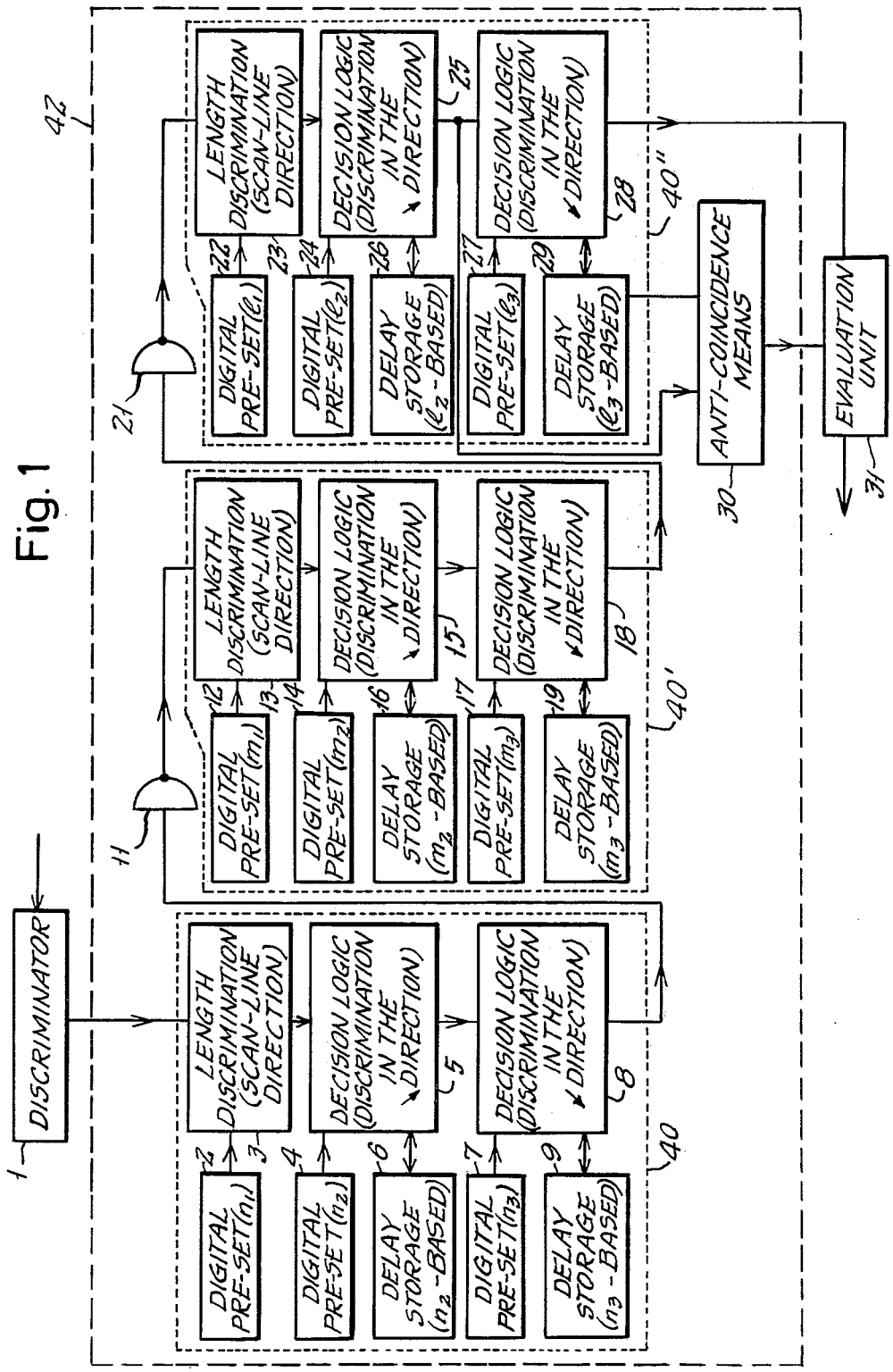
FIG. 1 is a block diagram of circuitry representing an illustrative embodiment of the invention.

In FIG. 1, 1 identifies a discriminator, which may be as described in detail in said U.S. Pat. No. 3,967,053. Discriminator 1 supplies oscillator-derived binary signals which are associated with individual raster elements of the image. These signals are fed as first signals to a length discriminator 3 responsive to length in the scan-line direction. At discriminator 3, the first $n_1$ raster elements having the value L are suppressed, corresponding to the preset value $n_1$ (set digitally at 2), following each raster element having the value 0, thereby effecting an erosion of $n_1$ raster elements in the scan-line direction. The signals which have been changed in this way pass from discriminator 3 to a decision-logic device 5. It differs from the decision-logic device described in said U.S. Pat. No. 3,967,769 by the fact that it has no anti-coincidence means; also at logic device 5, only the delay means for length discrimination downward to the right is needed. The decision-logic device 5 effects (1) an erosion by $n_2$ raster elements downward to the right, as well as (2) a delay storage at 6, based on a preset value $n_2$, set digitally at 4. Thereupon, similar but further processing takes place in a decision-logic device 8 with delay storage at 9, based on a preset value $n_3$, set digitally at 7, serving to effect discrimination downward to the left.

In the circuitry thus-far described, signals representing all objects in the scanned image have experienced erosion, in each of the three directions indicated; and the overall circuitry to effect this result will be referred to as erosion circuit module 40. And it will be noted that what has thus-far been described has been previously described in said U.S. Pat. No. 3,967,053, where the purpose was to serve for proper counting of particles, and to determine the dispersion of particles; in the present case, however, the components of module 40 serve an entirely different ultimate function, as will become clear.

For the present purposes, the erosion at 40 causes the disappearance (from the scanned image) of objects whose length in the three directions of discrimination is not greater than corresponds to the values $n_1$, $n_2$ and $n_3$.

In the circuit arrangement of the invention, those image signals which survive erosion in module 40 are passed through an inverter 11 which inverts all image signals, before passing them to a second erosion circuit module 40', which may be in all respects as described for module 40; the output of module 40' being to a second inverter 21.

By reason of the inversion at 11, the signals presented to erosion module 40' are the inverse (or negative) of image signals, so that their erosion in the processing circuitry of module 40' will have performed an overall dilation, as the eroded inverted signals emerge (after second inversion at 21) in the form of thus-processed image signals; in other words, the image signals at the output of the second inverter 21 have been effectively dilated, as compared to those entering the first inverter 11. The dilation is effected in the scan-line direction by length discriminator 13, based on a digital preset value $m_1$ set at 12; by a decision-logic device 15 with delay storage at 16 and a digital preset value $m_2$ set at 14, for discrimination downward to the right; and by a decision-logic device 18 with delay storage at 19 and a digital preset value $m_3$ set at 17, for discrimination downward to the left. The digital preset values $m_1$, $m_2$ and $m_3$ are so fixed on basis of experience (as a function of other parameters of the instrument) that, in the illustrative example of identifying metaphase plates, the image chromosomes corresponding to a metaphase plate "aggregate". These aggregated metaphase plates are considerably larger than any remaining cells or impurities, which have also dilated, as can be seen by reference to FIG. 3, wherein areas within solid lines represent particles viewed in their originally scanned state, and wherein the same subject matter after the described dilation is represented by extended areas which are completed by heavy dashed lines; more specifically, a cell 60 within the field of the originally scanned image will, after surviving selection by erosion processing at 40, and after dilation at 11-40'-21, appear in the resulting image as a dilated cell 62, and a metaphase plate 61 which appeared in the same originally scanned field as a plurality of discrete small objects (chromosomes) will appear in the dilated situation as a single large-area agglomeration 63.

Figure 3:
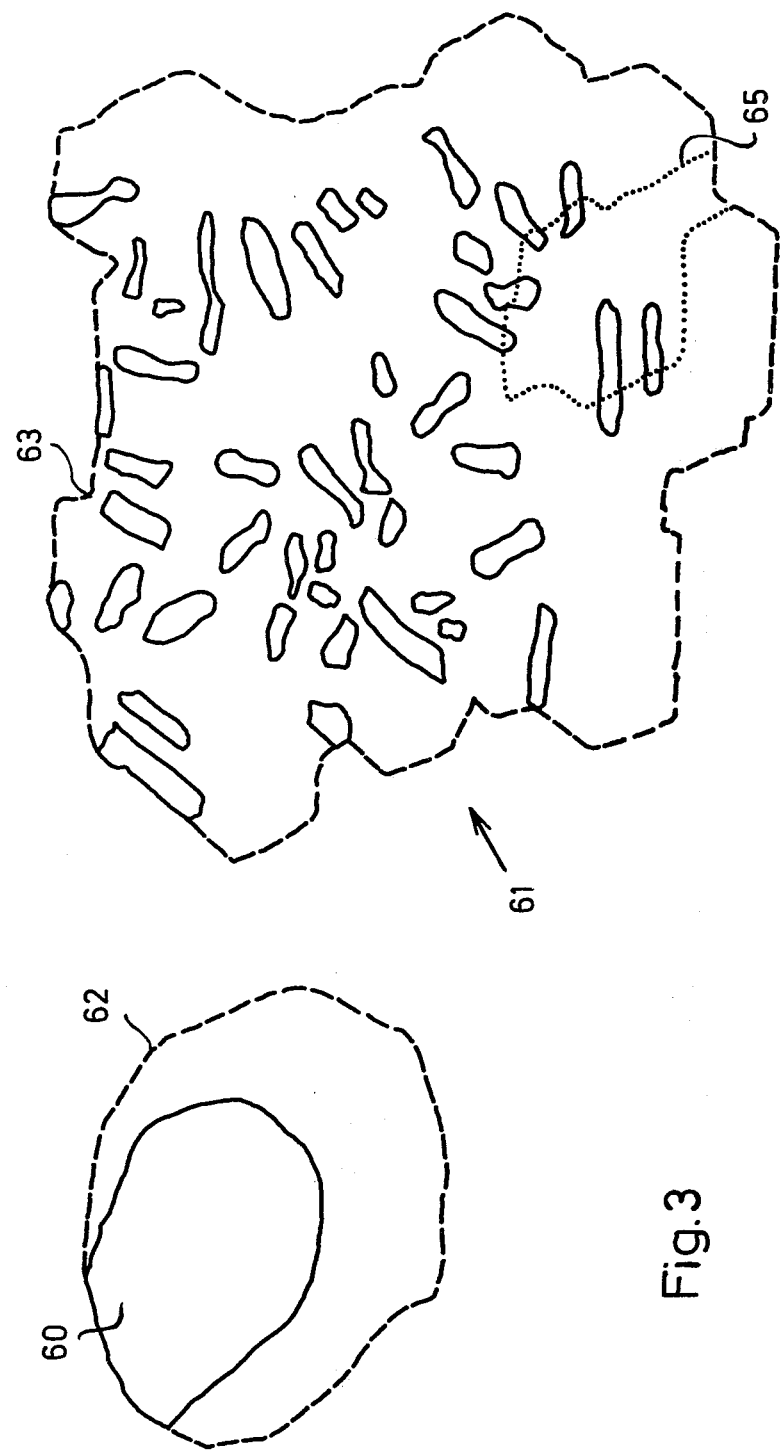
FIG. 3 is a diagram showing the effect of electronic dilation and erosion on images of cells and metaphase plates.

In the third part of the circuit, which may be a third module 40'', similar to modules 40 and 40', following inversion at 21, erosion is again performed so that only aggregated metaphase plates remain in the image. This is effected in the scan-line direction by a length discriminator 23, based on a digital preset value $l_1$ st at 22; by a decision-logic device 25 with delay storage at 26 and a digital preset value $l_2$ set at 24, for discrimination downward to the right; and by a decision-logic device 28 with delay storage at 29 and a digital preset value $l_3$ set at 27, for discrimination downward to the left. The digital preset values $l_1$, $l_2$ and $l_3$ are also established on the basis of experience. In FIG. 3, the condition present in the surviving image signals, i.e., after erosion at module 40'', is shown by the area 65 which is completed by dots; the cell has disappeared, but from the original metaphase plate 61 there remains an area 65 which is a measure of the quality of the metaphase plate.

Anticoincidence means 30 may be employed to determine that a metaphase plate has been completely identified in the scanned image and such anticoincidence means is known, for example, from said U.S. Pat. No. 3,967,053. Inputs to means 30 are shown connected to the delay storage device 29 and to the input of the decision-logic device 28 (or to the output thereof, which in this case does not make any difference). The output of anti-coincidence means 30 is connected with the evaluation unit 31, as is also the output of decision-logic device 28. From there, a reporting signal goes to a control unit 43, which will be discussed below in conjunction with FIG. 2. It will be understood that, in addition, a size determination may be made of the areas of agglomerated metaphase plates, within the evaluation unit 31, again in known manner as described in said Provisional Patent, and that this further information may also be forwarded to the control unit 43.

In general, the digital preset values in each of the three circuit modules 40-40'-40'' can be the same, i.e., $n_1 = n_2 = n_3$, $m_1 = m_2 = m_3$, and $l_1 = l_2 = l_3$. In such a situation, the erosions or dilations in all three directions are the same, within any given module.

It will be understood that the circuit arrangements of the present invention are in no way limited to erosion or dilation in three directions. For example, it is also possible, and in many cases sufficient, to limit onself to two directions, namely to length discrimination in the scan-line direction and in the direction perpendicular thereto. In such case, a decision-logic device (including its associated delay storage and input for the digital preset value) can be eliminated from each circuit module for erosion or dilation. Furthermore, the raster elements of the individual lines need no longer be shifted with respect to each other, so that as a whole, a considerably simpler construction results. On the other hand, it is also possible to use more than three directions for erosion and dilation, in which case, the construction becomes correspondingly more complex.

In one advantageous embodiment of the present invention, only two circuit modules, namely for dilation and erosion (i.e., modules 40' and 40") are used instead of the described three circuit modules (for erosion, dilation and erosion) in FIG. 1. Such considerable simplification is possible whenever the preparations contain only a few particles of impurities, or if the impurity particles do not interfere with the search for metaphase plates.

Figure 2:
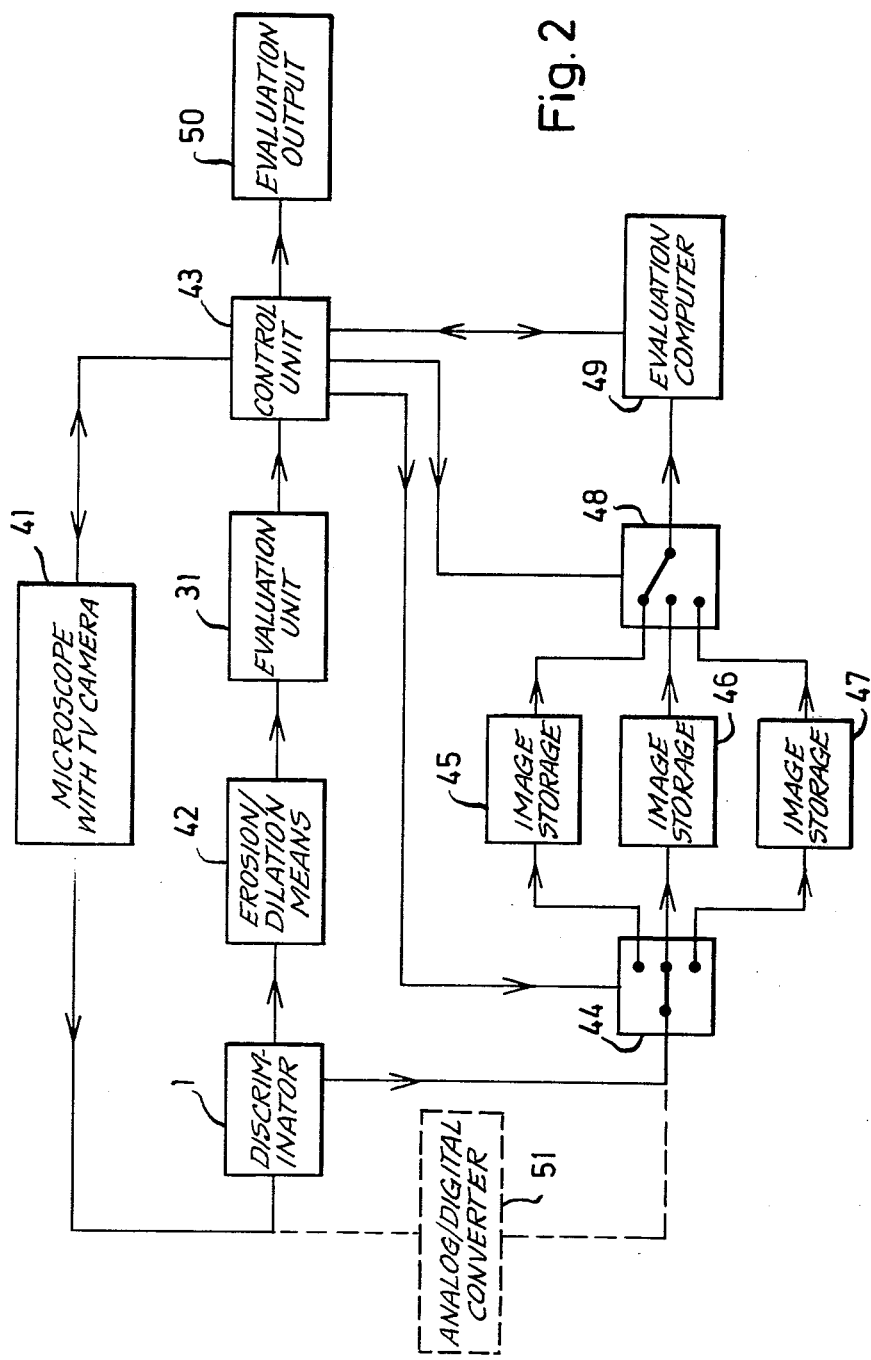
FIG. 2 is a block diagram of an entire measurement apparatus, incorporating the circuitry of FIG. 1.

FIG. 2 is a block diagram of an illustrative embodiment of the entire measurement system, wherein the described circuit arrangement of FIG. 1 is identified at 42. A microscope 41 includes a scanning device (such as a television camera or flying-spot laser beam). All controls required for scanning the microscope image and for the entire measurement system are provided by a control unit 43. Output signals from the scanning device 41 are fed to the discriminator 1, converted into binary signals and then processed further in the erosion/dilation circuit means 42. The binary signals from discriminator 1 also pass via a switch 44 to one of a plurality of image-storage devices 45, 46, 47. Upon commencement of an examination, switch 44 is first of all so set by control unit 43 that the image-storage device 45 is connected. As soon as the described evaluation unit 31 has found a metaphase plate, it issues a report to this effect to the control unit 43, the coordinates of the metaphase plate being first of all stored in control unit 43. At the same time, an evaluation computer 49 receives a signal to examine the metaphase plate more carefully. For this purpose, and after control unit 43 has actuated switch 48 for connection to the image-storage device 45, the corresponding region of the image storage may be transferred into storage means associated with computer 49; alternatively, the evaluation computer 49 can have recourse to the information in the image-storage device 45 during the entire evaluation process. When the image in which a metaphase plate has been found has been completely scanned, control unit 43 actuates switch 44 for connection to the next image-storage device, i.e., to storage device 46 in the present case. The image-storage device 45 is only released for storage of a new image when the evaluation computer 49 no longer requires any information from the stored image at 45. It will be understood that control unit 43 is so designed that several metaphase plates may be accommodated and evaluated from within a single image field.

For applications in which metaphase plates occur only rarely, use of a single image-storage device (e.g., device 45 alone) has the advantage that upon detection of a metaphase plate, the scanning process for evaluation by computer 49 need not be re-initiated but can continue to run, so that time is saved. In this case, switches 44 and 48 are superfluous, and control unit 43 causes the image stored at 45 to become replaced by the next image only if the evaluation computer 49 does not require any more information; if it were otherwise, the scanning process would be interrupted. For applications in which metaphase plates are frequently found, use of a plurality of image-storage devices provides the advantage that the scanning process need be rarely interrupted, thus assuring little loss of time.

For special applications, it may be advantageous not to have the image-storage device or devices store only black-and-white images. In that case, the scanned image signals are fed to the image-storage device or devices not by discriminator 1 but by an analog-digital converter 51 which may be coupled directly to the output of the scanner at 41.

Control unit 43 and evaluation computer 49 can be combined in a process computer which may also contain evaluation unit 31. And another output of control unit 43 may transfer the evaluation to a display or other utilization device, such as a printer at 50.

What is claimed is:

1. A method of detecting accumulations of particles, for instance metaphase plates, in an image converted by a raster process into electrical signals in which the image is subdivided by a high-frequency signal into raster elements which have a fixed position with respect to each other in successive scanning lines and in which there are provided a discriminator for the selection of the objects to be evaluated in accordance with selectable criteria, an evaluation unit for the logical analysis and counting of the objects, delay storages for comparison of adjacent raster elements in successive scanning lines, said storages delaying the digital image signals fed by amounts of time which correspond to one raster element spacing and approximately one line length, and a decision logic in order to determine whether a structure element fits the object examined, characterized by the fact that an electronic image dilation is carried out in several directions, the parameters of the dilations being so selected that the images of the chromosomes of metaphase plates agglomerate to form uniform structures, and that thereupon an image erosion is effected in several directions the parameters of the erosion being so selected that images of cells disappear while images of the agglomerated metaphase plates, however, remain.

2. A method according to claim 1, characterized by the fact that prior to the dilation an erosion is carried out the parameters of which are so selected that at least by far the greatest part of the impurities disappear but the chromosomes are retained.

3. An arrangement for the carrying out of the method according to claim 1, characterized by the fact that behind the output of the discriminator (1) a circuit for a dilation in at least two directions and a circuit part (40") for an erosion in at least two directions are arranged.

4. An arrangement for the carrying out of the method of claim 2, characterized by the fact that behind the output of the discriminator (1) a circuit part (40) for an erosion in at least two directions, a circuit for a dilation in at least two directions and a circuit part (40") for an erosion in at least two directions are provided.

5. An arrangement according to claim 3 or 4, characterized by the fact that the circuit for the dilation consists of an inverter, a circuit part (40') and an inverter.

6. An arrangement according to claim 3 or 4, characterized by the fact that an anti-coincidence member (30) and an evaluation unit (31) are arranged behind the last circuit part (40).

7. An arrangement according to claim 3 or 4, characterized by the fact that the circuit parts (40) consist of a length discriminator in line direction (3, 13, 23) with inputtable digital preset value and a decision logic (5, 15, 25) with corresponding delay storage and inputtable digital preset value and guide value for the scanning direction downward.

8. An arrangement according to claim 3 or 4, characterized by the fact that the circuit parts (40) consist of a length discriminator in line direction (3, 13, 23) with inputtable digital preset value, a decision logic (5, 15, 25) with corresponding delay storage and inputtable digital preset value and guide value as well as a delay member for the scanning direction downward to the right and a decision logic (8, 18, 28) with corresponding delay storage and inputtable digital preset value and guide value as well as a delay member for the scanning direction downward to the left.

9. An arrangement according to claim 8, characterized by the fact that the circuit parts (40, 40', 40'') contain further decision logics and that the delay members of the decision logics are so dimensioned that the erosion or dilation is carried out in more than three directions.

10. An arrangement according to claim 3 or 4, characterized by the fact that the inputs of an anticoincidence member (30) are connected with the input of the last decision logic (28) and with the output of the corresponding delay storage (29) and that the output of the anticoincidence member (30) is connected with the input of the evaluation unit (31).

11. An arrangement according to claim 3 or 4, characterized by the fact that the output of the discriminator (1) is connected in addition with the input of an image storage (45) and that the output of the image storage (45) is connected, for the transfer of the image information when the evaluation unit (31) has found a metaphase plate, to an evaluation computer (49).

12. An arrangement according to claim 11, characterized by the fact that the output of the discriminator (1) is connected via a switch (44) with a plurality of image storages (45, 46, 47) and that the input of the evaluation computer (49) is connected via a switch (48) with the outputs of the image storages (45, 46, 47).

13. An arrangement according to claim 11 or 12, characterized by the fact that instead of the discriminator (1) the receiver of the scanning device (41) is connected via an analog-digital converter (51) to one or more image storages.

14. An arrangement according to claim 3 or 4, characterized by the fact that a control unit (43) carries out one or more of the following functions:
(a) control of the scanning table of the microscope;
(b) control of the television camera or the laser-beam scanning device;
(c) upon the detection of a metaphase plate, the taking over of the coordinates of the scanning table and of the coordinates of the metaphase plate within the image and output of these data;
(d) output of the evaluation of the metaphase plate by the evaluation unit (31) or control of the evaluation computer (49) for the more precise examination of the metaphase plate and output of the result from the evaluation computer (49);
(e) connection of the inputs of the image storages (45, 46, 47) to the discriminator output (1) or to the receiver output via an analog-digital converter (51);
(f) connection of the outputs of the image storages (45, 46, 47) to the evaluation computer (49).

15. An arrangement according to claim 14, characterized by the fact that control unit (43), evaluation computer (49) and evaluation unit (31) are combined in a process computer.

16. The method of selecting, for evaluation or other purposes, a cluster of discrete small elements from among other particles within a given field of view, which method comprises scanning the field by a raster process to develop an electrical-image signal in which scan lines in the image are subdivided into raster elements which have fixed position with respect to each other in successive scan lines, subjecting the electrical-image signal to electronic discrimination in each of a plurality of different directions to select the objects in accordance with selected criteria, such discrimination comprising (1) an electronic erosion wherein the images of all objects smaller than a given size are eliminated from the electrical-image signal to produce an eroded electrical-image signal characteristic of the scanned field, said given size being selected to be smaller than the size of the elements of the cluster, (2) inverting the eroded electrical-image signal and performing a second electronic erosion wherein intermediate areas are eroded between objects in the eroded-image field, the extent of second electronic erosion being selected to be at least the anticipated space between discrete elements in a single cluster, (3) inverting the electrical-image signal after such intermediate-area erosion, whereby a dilated electrical-image signal is produced wherein the small-element images have been agglomerated into a single cluster of size larger than such dilated other-size particle images as remain in the image-field signal, and (4) performing an electronic erosion on the dilated electrical image signal, the extent of the erosion being so selected as to eliminate from the imaged-field signal such dilated-object image sizes as are greater than dilated other-particle size but less than the size of agglomerated clusters of the small elements.

17. The method of selecting, for evaluation or other purposes, a cluster of discrete small elements from among other particles within a given field of view, wherein the other particles are smaller than the size of the cluster, which method comprises scanning the field by a raster process to develop an electrical-image signal in which scan lines in the image are subdivided into raster elements which have fixed position with respect to each other in successive scan lines, and subjecting the electrical-image signal to electronic discrimination in each of a plurality of different directions to select the objects in accordance with selected criteria, such discrimination comprising (1) inverting the electrical-image signal and performing an electronic erosion wherein intermediate areas are eroded between objects in the field, the extent of the electronic erosion being selected to be at least the anticipated space between discrete elements in a single cluster, (2) inverting the electrical-image signal after such intermediate-area erosion, whereby a dilated electrical-image signal is produced wherein the small-element images have been agglomerated into a single cluster of size larger than such dilated other-size particle images as remain in the imaged-field signal, and (3) performing an electronic erosion on the dilated electrical image signal, the extent of the erosion being so selected as to eliminate from the imaged-field signal such dilated-object image sizes as are greater than dilated other-particle size but less than the size of agglomerated clusters of the small elements.

18. The method of selecting, for evaluation or other purposes, a cluster of discrete small elements from among other particles within a given field of view, which method comprises scanning the field by a raster process to develop an electrical-image signal in which scan lines in the image are subdivided into raster elements which have fixed position with respect to each other in successive scan lines, and subjecting the electrical-image signal to electronic discrimination in each of a plurality of different directions to select the objects in accordance with selected criteria, such discrimination comprising (1) an electronic erosion wherein the images of all objects smaller than a given size are eliminated from the electrical-image signal to produce an eroded electrical-image signal characteristic of the scanned field, said given size being selected to be smaller than the size of the elements of the cluster, (2) inverting the eroded electrical-image signal and performing a second electronic erosion wherein intermediate areas are eroded between objects in the eroded-image field, the extent of second electronic erosion being selected to be at least the anticipated space between discrete elements in a single cluster, and (3) inverting the electrical-image signal after such intermediate-area erosion, whereby a dilated electrical-image signal is produced wherein the small-element images have been agglomerated into a single cluster of size larger than such dilated other-size particle images as remain in the imaged-field signal.

* * * * *